United States Patent
Klepp

(10) Patent No.: US 10,429,382 B2
(45) Date of Patent: Oct. 1, 2019

(54) IMMUNOLOGICAL TEST ELEMENT WITH CONTROL ZONE FOR IDENTIFYING HOOK EFFECT

(71) Applicant: Roche Diagnostics Operations, Inc., Indianapolis, IN (US)

(72) Inventor: Juergen Klepp, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 118 days.

(21) Appl. No.: 15/348,582

(22) Filed: Nov. 10, 2016

(65) Prior Publication Data

US 2017/0059564 A1 Mar. 2, 2017

Related U.S. Application Data

(63) Continuation of application No. 14/584,382, filed on Dec. 29, 2014, now Pat. No. 9,528,986, which is a
(Continued)

(30) Foreign Application Priority Data

Jan. 14, 2006 (EP) ..................... 06000791

(51) Int. Cl.
*G01N 33/543* (2006.01)
*G01N 33/558* (2006.01)

(52) U.S. Cl.
CPC . *G01N 33/54386* (2013.01); *G01N 33/54306* (2013.01); *G01N 33/54366* (2013.01);
(Continued)

(58) Field of Classification Search
CPC ............. G01N 33/54306; G01N 33/54366
See application file for complete search history.

(56) References Cited

U.S. PATENT DOCUMENTS

| 4,861,711 A | 8/1989 | Friesen et al. |
| 5,118,609 A | 6/1992 | Baier et al. |

(Continued)

FOREIGN PATENT DOCUMENTS

| WO | 88/08534 | 11/1988 |
| WO | WO200031538 | 6/2000 |

(Continued)

OTHER PUBLICATIONS

Frens, G., "Controlled Nucleation for the Regulation of the Particle Size in Monodisperse Gold Suspension", Natura Physical Science, vol. 241, Jan. 1, 1973, pp. 20-22.
(Continued)

*Primary Examiner* — Erik B Crawford
(74) *Attorney, Agent, or Firm* — McDonnell Boehnen Hulbert & Berghoff LLP

(57) ABSTRACT

The invention concerns a test element for carrying out an immunological sandwich test for determining an analyte from a liquid sample containing a reagent zone or conjugate zone which contains a conjugate of an analyte binding partner and a label which can be detected directly or indirectly by visual, optical or electrochemical means (e.g. an enzyme, fluorescent or direct label etc.) wherein said conjugate can be dissolved by the liquid sample, a detection zone which contains a permanently immobilized (i.e. which cannot be detached by the liquid sample) binding partner for the analyte or for complexes containing the analyte; and a control zone which contains a permanently immobilized binding partner for the conjugate of analyte binding partner and label characterized in that the control zone additionally contains one or more permanently immobilized binding partner(s) for the analyte or for complexes containing the analyte.

11 Claims, 1 Drawing Sheet

Related U.S. Application Data continuation of application No. 12/881,651, filed on Sep. 14, 2010, now Pat. No. 8,951,806, which is a continuation of application No. 11/622,515, filed on Jan. 12, 2007, now abandoned.

(52) U.S. Cl.
CPC .... *G01N 33/558* (2013.01); *B01L 2300/0825* (2013.01); *B01L 2400/0406* (2013.01)

(56) References Cited

U.S. PATENT DOCUMENTS

| | | |
|---|---|---|
| 5,296,347 A | 5/1994 | Lamotte |
| 5,451,504 A | 9/1995 | Fitzpatrick et al. |
| 5,480,792 A | 1/1996 | Buechler et al. |
| 5,939,272 A | 8/1999 | Buechler et al. |
| 5,968,839 A | 10/1999 | Blatt et al. |
| 6,156,270 A | 12/2000 | Buechler |
| 6,183,972 B1 | 2/2001 | Kuo et al. |
| 6,528,323 B1 | 3/2003 | Thayer et al. |
| 7,745,158 B2 | 6/2010 | Phillips et al. |
| 2002/0055126 A1 | 5/2002 | Schaffler et al. |
| 2005/0118662 A1 | 6/2005 | Spinke et al. |
| 2006/0246600 A1 | 11/2006 | Yang et al. |
| 2006/0246601 A1 | 11/2006 | Song et al. |
| 2007/0134811 A1 | 6/2007 | Takeuchi et al. |
| 2007/0259450 A1 | 11/2007 | Bodenbach et al. |

FOREIGN PATENT DOCUMENTS

| | | |
|---|---|---|
| WO | WO200077524 | 12/2000 |
| WO | 2004109285 | 6/2004 |
| WO | WO2005111607 A2 | 11/2005 |

OTHER PUBLICATIONS

Roth, J., "The Colloidal Gold Marker System for Light and Electron Microscopic Cytochemistry", Immunocytochemistry 2, ISBN 0 12 404021, 1983, pp. 218-284.

Vallins, et al., "Molecular cloning of human cardia troponin I using polymerase chain reaction", FEBS, 270:57-61 (1990).

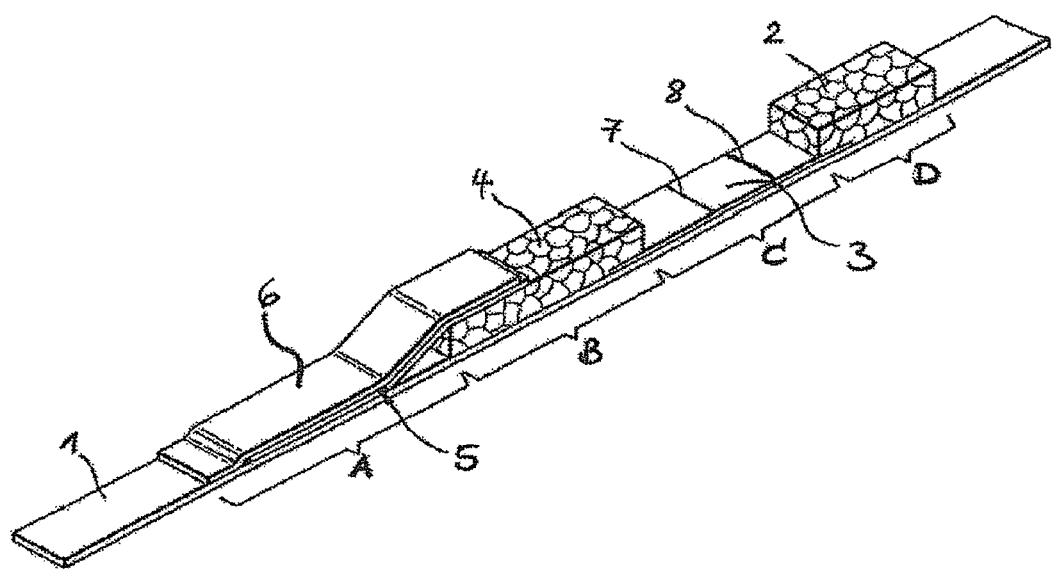

IMMUNOLOGICAL TEST ELEMENT WITH CONTROL ZONE FOR IDENTIFYING HOOK EFFECT

BACKGROUND OF THE INVENTION

The present invention refers generally to diagnostic test devices and, more particularly, to a test element for carrying out an immunological sandwich test for the determination of an analyte from a liquid sample comprising a novel control zone.

Diagnostic assays for analyzing liquid samples such as blood, serum, plasma, urine, saliva, sweat, etc., often contain a control mechanism winch should ensure the proper performance of the test and its functionality.

A control mechanism which is internal to the test is rather unusual when carrying out diagnostic tests on automated laboratory instruments since the instrument itself usually ensures and/or monitors that the test is carried out properly. In the case of automated laboratory instruments the pipetting volumes or the incubation times and other parameters are for example usually automatically monitored by the automated analyzer. The functionality of the test (with regard to the reagents as well as with regard to the instruments) is usually ensured by additionally determining control samples within a series of measurements.

In a point-of-care (PoC) environment, i.e., in the case of patient sample measurements outside of a specialized laboratory, single determinations are often carried out. The test elements used for this usually contain dried reagents which are redissolved by the sample and thus reactivated for the actual analysis. Immunological test elements such as immunochromotographic test strips or immunological capillary gap test elements have proven to be useful in the PoC environment especially in the field of immunoassays. The immunological test elements are often based on optically detectable reactions that are usually evaluated visually or by means of a measuring instrument (reader). In this case the person carrying out the test has a special responsibility since some functions that are carried out by automated laboratory instruments in the case of wet chemistry tests have to be taken care of by the person carrying out the test (for example pipetting the correct sample volume or adherence to the assay time).

However, the personnel carrying out the test in a PoC environment are usually not specially trained employees. Tests in the PoC field are frequently carried out by doctors, nurses, doctor's assistants, pharmacists or by the patients themselves. In contrast, in specialized laboratories (e.g., central laboratories in hospitals, large laboratories) the assays are carried out by specially trained technical assistants (e.g., MTA).

Therefore, test suppliers have developed so-called onboard-controls for these special "decentral" or PoC applications which respond to major handling errors (such as underdosing) when performing the tests and/or to test malfunctions and thus make the user aware of an invalid test result.

In the special case of immunological test elements which function according to the so-called sandwich principle, "on-board controls" are usually implemented in the form of control lines or zones (both terms are used synonymously in the following).

These control lines or zones serve in the ideal case to ensure that the user recognizes that sufficient sample volume has been applied for correct test performance, that the immunochemical reagents that are impregnated or dried in the test element were still present in a migratable form (i.e., in a form that can be moved in the test element) and that the immunological activity of the reagents that are critical for function was still present within a certain range. Otherwise the control line or the control zone allows incorrect test performance or the unusability of the test element to be recognized and thus helps to prevent false test results from being obtained.

A typical test structure is as follows:

A conjugate zone (also: reagent zone) is usually located in or on the test element between a sample application zone and a detection zone. The sample application zone and conjugate zone can also be identical. The conjugate zone contains an immunological binding partner (typically an antibody or a fragment thereof) that is directed against the analyte and can be redissolved and redetached and thus mobilized by the sample liquid. The binding partner is usually conjugated (so-called conjugate) to a signal-generating enzyme or a so-called direct label (e.g., gold or colored latex particles, fluorescent labels).

The detection zone contains an irreversibly immobilized second independent binding partner directed against the analyte (or a complex formed from the analyte).

If the analyte is present in the sample, it thus accumulates in the detection zone in the form of a so-called sandwich (i.e., an immunological complex of immobilized binding partner, analyte and signal-generating binding partner) and becomes visible, optionally after the addition of further reagents.

In the case of the streptavidin-biotin principle (as a representative of the so-called indirect sandwich principle) the second binding partner is also located in the conjugate zone in the form of a mobilizable biotin conjugate. The detection zone contains irreversibly immobilized streptavidin.

Excess conjugate of binding partner and label or biotin is transported together with the sample into a waste (suction zone, which serves to take up excess sample) that is located "downstream" of the detection zone.

The control zone is usually located between the detection zone and waste.

The following functional principles for control zones are known to a person skilled in the art and are described with their advantages and disadvantages:

1. Analyte Control Zone

The control zone located between the detection zone and the waste contains irreversibly immobilized analyte (or an analyte analogue). Excess binding partner-label conjugate is bound to the immobilized analyte or analyte analogue and thus leads to a detectable signal at the control line.

This mechanism is nowadays often covered by polyhapten control zones and therefore the advantages and disadvantages are described in more detail in section 2.

A special disadvantage of the analyte control line is that it is often difficult and laborious to produce the analyte (e.g., an antigen in sufficient quantities).

2. Polyhapten Control Zone

The control zone situated between the detection zone and the waste contains a polyhapten directed against the conjugate antibody.

Advantage: In addition to ensuring that the reagents were able to migrate and providing a control for the correct sample volume, the formation of a signal in the control zone also ensures the immunological activity of the conjugate of analyte binding partner and label.

Disadvantage: At high analyte concentrations in the sample the ability of the binding partner-label conjugate to bind antigen is already saturated before reaching the control zone and the polyhapten in the control zone can capture no more conjugate. Consequently the control mechanism fails.

In this case the user must falsely assume that the test result in the detection zone is invalid.

This is particularly frequently a disadvantage when a wide concentration range has to be covered between the cut-off value of the test (i.e., the lower limit or the measuring range) and the upper concentration range. This is for example the case for pregnancy tests in which the hormone hCG has to be detected in urine at a cut-off of about 10-20 mIU/ml and, on the other hand, hCG values of up to 500,000 mIU/ml are also observed at the end of the first trimester of pregnancy. Such high analyte concentrations result in negative results in the control zone and thus misleadingly simulate an invalid test result in the detection zone.

3. Anti-IgG Control Zone (as a Form of an Indirect Control Zone)

The control zone contains an antibody directed against the antibody-label conjugate. This control zone principle is very widespread in pregnancy test strips.

Example: If an analyte-specific, labelled mouse antibody is used, the control zone contains for example a polyclonal antibody directed against mouse antibody (e.g., PAB<mouse Fcγ>S-IgG).

Advantage: The formation of the control line is not influenced by high analyte concentrations in the sample.

Disadvantage: The correct immunological activity of the conjugate is not detected by this mechanism. This has recently led to discussions with the approval authorities e.g. the FDA in the USA, with regard to new approvals of test elements. Another disadvantage is that when interference-eliminating antibodies are used in assays which use blood, the intensity of the signal in the control zone is greatly reduced. Interference-eliminating antibodies are usually used in the test in a 10 to 500-fold excess relative to the analyte-specific conjugate antibody. Unconjugated antibodies of the same species are usually used as interference-eliminating antibodies which are thus also captured by the control line.

If the analyte is present in the sample, a large portion of the conjugate already binds in the detection zone and, therefore, low residual amount of conjugate leads to a complete failure of the control zone in the presence of the interference eliminating antibody.

4. Indirect Control Line that is Not Affected by Interference-Eliminating Antibodies The control line contains a binding partner which is directed against an "independent label" of the conjugate.

Example: The analyte-specific binding partner of the conjugate is additionally digoxigenylated and captured at the control line by means of an anti-digoxigenin antibody (cf., for example, US-A 2002-0055126).

Advantage: The binding capability of the control line is not reduced by high analyte concentrations. Furthermore the binding capability of the control line is not reduced by the presence of interference-eliminating antibodies.

Disadvantage: The antibodies of the conjugate have to be additionally specially modified which results in additional effort, cost and time. Furthermore the control line can again fail when there is a high endogenous content of the selected label.

SUMMARY OF THE INVENTION

It is against the above background that the present invention provides certain unobvious advantages and advancements over the prior art. In particular, the inventors have recognized a need for an improved control line mechanism.

Although the present invention is not limited to specific advantages or functionality, it is noted that the present invention provides a control mechanism for immunological test elements which reliably functions over a wide concentration range of the analyte independently of the components of the test formulation (especially with regard to the use of so-called interference-eliminating antibodies) without being affected by endogenous sample components.

In accordance with one embodiment of the present invention, a test element for carrying oat an immunological sandwich test for determining an analyte from a liquid sample is provided comprising a reagent zone, a detection zone, and a control zone. The reagent zone contains conjugate of an analyte binding partner and a label which can be detected directly or indirectly by visual, optical or electrochemical means, wherein the conjugate can be dissolved by the liquid sample. The detection zone contains a permanently immobilized binding partner for the analyte or for complexes containing the analyte. The control zone contains a permanently immobilized binding partner for the conjugate of analyte binding partner and label, wherein the control zone additionally contains one or mote permanently immobilized binding partner(s) for the analyte or for complexes containing the analyte.

In accordance with another embodiment of the present invention, a method for detecting analyte from a liquid sample is provided comprising: applying a sample to a test element; reacting an analyte present in the sample with a labelled conjugate to form an analyte-conjugate complex; binding the analyte-conjugate complex in the detection zone to the permanently immobilized binding partner for the analyte or for complexes containing the analyte; binding the labelled conjugate that has not reacted with the analyte in the control zone to the permanently immobilized binding partner for the conjugate, and binding the analyte-conjugate complex in the control zone to the permanently immobilized binding partner for the analyte or for complexes containing the analyte.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated by like reference numerals and in which:

FIG. 1 schematically shows an embodiment of a test element according to the invention in the form of an immunochromotographic test strip.

The numbers and letters in the FIGURE denote:
A sample application and conjugate zone
B erythrocyte separation zone
C detection zone
D suction zone
1 support material
2 suction fleece (waste)
3 chromatography membrane with detection line and control line
4 erythrocyte separation matrix (blood separation fleece)

5 gold conjugate fleece (labelled conjugate)
6 biotin conjugate fleece (tagged conjugate)
7 detection line (immobilized polystreptavidin)
8 control line Skilled artisans appreciate that elements in the FIGURE are illustrated for simplicity and clarity and have not necessarily been drawn to scale. For example, the dimensions of some of the elements in the FIGURE may be exaggerated relative to other elements to help improve understanding of the embodiment(s) of the present invention.

DETAILED DESCRIPTION OF THE INVENTION

In accordance with one embodiment, the invention firstly concerns a test element for carrying out an immunological sandwich test for determining an analyte from a liquid sample as is in principle known from the prior art in many variants with the exception of the novel control zone. For example, the test element can be essentially composed of absorbent materials such as fleeces, membranes, papers, etc. (cf., for example, U.S. Pat. No. 4,861,711, US-A 2002-0055126, WO 2005/111607) or the liquid transport may be effected by microfluidic structures (partially also driven by the action of external forces such as suction, pressing, centrifugation) or capillary channels (cf., for example, U.S. Pat. No. 6,156,270).

The test element contains a reagent zone which contains a conjugate of an analyte binding partner (typically an antibody or an immunologically active antibody fragment capable of analyte binding if the analyte is an antigen or hapten, or an antigen or hapten if the analyte is an antibody) and a label which can be detected directly or indirectly by visual, optical or electrochemical means, wherein the conjugate can be dissolved by the liquid sample. Suitable labels are, for example, enzymes, fluorescent labels, electrochemically active groups or so-called direct labels such as metal or carbon labels or colored latices. This zone is also referred to as the conjugate zone.

The conjugate zone can serve as a sample application zone or a separate sample application zone can be located before or after the conjugate zone. The conjugate zone can, in addition to the conjugate of analyte binding partner and label described above, also contain an additional conjugate of a second analyte binding partner (which is in turn typically an antibody or an immunologically active antibody fragment capable of analyte binding) and a tagging substance which is itself a partner in a binding pair. The tagging substance can for example be biotin or digoxigenin and can be used to immobilize a sandwich complex consisting of labelled conjugate, analyte and tagged conjugate in the detection and/or control zone.

The test element additionally comprises a detection zone which contains a permanently immobilized binding partner (i.e., one that cannot be detached by the liquid sample) for the analyte or for complexes containing the analyte. The immobilized binding partner is in turn typically an antibody or an immunologically active antibody fragment capable of analyte binding or an antigen or (poly)hapten. If one of the above-mentioned tagged conjugates is used which for example carry biotin or digoxigenin together with an analyte binding partner, the immobilized binding partner can also be streptavidin or polystreptavidin and an anti-digoxigenin antibody.

Finally, there is a control zone in or on the test element which contains a permanently immobilized binding partner for the conjugate of analyte binding partner and label for example in the form of an immobilized polyhapten which acts as an analyte analogue and is able to bind the analyte binding partner from the labelled conjugate. It is important for the invention that the control zone additionally contains one or more permanently immobilized binding partner(s) for the analyte or for complexes containing the analyte. The latter binding partners can be selected from the same compounds which were described above in connection with the immobilized binding partners of the detection zone. These immobilized binding partners in the detection zone and in the control zone are typically identical. They may, however, also be different for example in that a binding partner for a biotin-tagged conjugate (hence, e.g., polystreptavidin) is immobilized in the detection zone and an anti-analyte antibody is immobilized in the control zone in addition to the polyhapten. In the latter case the anti-analyte antibody that is additionally immobilized in the control zone should be directed against (another) independent epitope and thus one that is not recognized by the conjugate antibodies (biotin-tagged conjugate and labelled conjugate).

Another embodiment of the invention is a method for detecting an analyte from a liquid sample with the aid of the test element according to the invention. The sample (which itself can be liquid or—if it is not itself a liquid—is dissolved or suspended in a liquid (e.g., buffer) and can thus be used) is applied to the test element and when it reaches the reagent zone (conjugate zone) it dissolves the reagents that are present there in a migratable form. The analyte—if it is present in the sample—is brought into contact with the labelled conjugate in the conjugate zone and reacts to form an analyte-conjugate complex. The mixture of sample and reagent subsequently reaches the detection zone where at least a portion of the analyte-conjugate complexes binds to the permanently immobilized binding partner for the analyte or for the complexes containing the analyte. Labelled conjugate which has not reacted with the analyte binds in the control zone to the permanently immobilized binding partner for the conjugate. In addition, the portion of the analyte-conjugate complexes which was not captured in the detection zone binds in the control zone to the permanently immobilized binding partner for the analyte or for the complexes containing the analyte.

The test strip shown in FIG. 1 corresponds to the Roche Cardiac T Quantitative Troponin test strip (Roche Diagnostics GmbH, Mannheim, Germany) with regard to structure and function with the exception of the control line according to the invention. Analogous test strips for determining other analytes are she obtainable (cf., for example, US-2005-0118662-A1 where a corresponding NT-proBNP test strip is described).

The following are located in succession on a plastic support material 1, i) a sample application zone A which has a fleece material 5 containing impregnated anti-analyte antibody-gold conjugate that can be detached therein and a fleece material 6 containing impregnated anti-analyte antibody-biotin conjugate that can be detached therein, ii) an erythrocyte separation zone B which contains a glass fibre fleece as an erythrocyte separation matrix 4 which is able to separate erythrocytes from whole blood and to produce substantially colorless blood plasma, iii) a detection zone C which contains a chromatography membrane 3 made of nitrocellulose in which or on which a polystreptavidin detection line 7 and a control line 8 are immobilized, and iv) a suction zone D containing a suction fleece which facilitates the migration of the sample through the chromatography membrane 3 and at the same time is used to receive the migrated sample as waste.

The anti-analyte antibody-gold conjugate (also referred to as labelled conjugate) in fleece 5 and the anti-analyte antibody-biotin conjugate also referred to as tagged conjugate) in fleece 6 serve to form the sandwich with the analyte; immobilized polystreptavidin in membrane 3 is used to form the detection line 7.

The control line 8 according to the invention in this case additionally contains a permanently immobilized binding partner for the complexes containing the analyte (i.e., in this case polystreptavidin) in addition to the permanently immobilized binding partner for the anti-analyte antibody-gold conjugate (i.e., an antibody-specific polyhapten (or analyte)).

As a result, the control line 8 captures the labelled conjugate directly and immuno-specifically mainly by means of polyhapten/analyte conjugate binding at low to medium analyte concentrations. In this case the streptavidin-biotin sandwich part of the control line 8 does not yet function since the small amount of formed sandwich is already almost quantitatively captured "upstream" by the detection line 7.

At high analyte concentrations the polyhapten conjugate binding mechanism of the control line 8 fails since the conjugate is already saturated with the analyte from the sample. However, in this case the conjugate present in the form of a sandwich complex (of labelled conjugate, analyte and tagged conjugate) is captured by the streptavidin-biotin mechanism of the control line 8. This works because for kinetic reasons the detection line 7 does not capture all the sandwich complex and the portions that chromatograph "downstream" are bound by the control line 8.

At extremely high analyte concentrations the so-called high dose Hook effect can occur in the sandwich format at detection line 7. The reason for this can be explained as follows: At limiting amounts of analyte (antigen deficiency relative to the amount of antibody present in the test element) an antigen molecule simultaneously binds both binding partners (labelled and tagged antibody) via independent epitopes. Hence the desired sandwich complex is formed and the analyte is bound to a binding partner which ensures immobilization in the detection zone 7 (in this case a biotinylated antibody which can bind to the streptavidin) as well as to a labelled binding partner (in this case gold-labelled antibody) which ensures the detectability of the analyte. At a high analyte excess (relative to the amount of labelled and tagged conjugate) both sandwich partners (i.e. labelled conjugate on the one hand and tagged conjugate on the other hand) each bind to two independently present analyte molecules such that although analyte is bound in the detection zone 7 by means of the tagged conjugate, it cannot be detected due to the absence of binding to a labelled conjugate.

If a high-dose Hook effect occurs at the detection line 7, then this simulates an analyte-negative test result despite the high analyte concentration. An analyte-independent control line 8 (for example based on an immobilized PAB<mouse Fcγ>S-IgG antibody) shows in this case a correct functioning of the test which ultimately leads to a false-negative test interpretation. In this case it would be desirable that the control line 8 is subject to the same high-dose Hook effect as the detection line 7 and that the test result would be indicated as invalid (and thus at least not false-negative) due to the simultaneous failure.

This is one of the advantages of the novel control line 8 of the invention. In particular, due to the high analyte concentration of the sample, there is almost no free labelled conjugate that reaches the control zone. This results in the part of the control line 8 that is based on the permanently immobilized binding partner for the labelled conjugate (in this case polyhapten), no longer finding a binding partner in the sample-reagent mixture. Consequently only the part of the control line 8 which is based on the permanently immobilized binding partner for the analyte or for the complexes containing the analyte (in this case the streptavidin-biotin mechanism) is still active. If sandwich formation is now prevented by the said high-dose Hook effect, the control line 8 also fails in addition to the detection line 7. The test result can then be recognized by the user as invalid and not erroneously as "negative".

The invention can not only be applied to the "indirect sandwich principle" described in detail above using the streptavidin-biotin binding. A generalisation to the "direct sandwich principle" is possible. In this case a sandwich partner is irreversibly immobilized in the detection line zone. Hence the control line contains the sandwich antibody immobilized in the detection line in addition to the polyhapten (directed against the conjugate antibody). It should be noted that in this case the alternative use of antigen instead of polyhapten as the immobilized binding partner in the control zone is not preferred since the sandwich antibody applied in the control line zone together with the antigen already forms an antigen-antibody complex and would thus at least partially "neutralize" both partial mechanisms of the novel control line. Hence it is preferable to use a polyhapten since this "synthetic epitope" is only directed against the migratable conjugate antibody but not against the second sandwich antibody. Hence it is able to function.

In order that the invention may be more readily understood, reference is made to the following examples, which are intended to illustrate the invention, but not limit the scope thereof.

Example 1

The invention is described in the following on the basis of a test strip for detecting cardiac troponin I (cTnI or abbreviated: TnI) from whole blood as an example.

a.) Analytical Element

Test strips according to FIG. 1 are manufactured.

The following were each attached slightly overlapping next to each other on a 5 mm wide and 78 mm long support foil 1 made of polyester (Melinex, 350 μm thick, from Imperial Chemistry Industries, GB) using hot-melt adhesive (Dynapol S 1358 from Hüls AG, Germany)

- a 1.5 mm thick and 7 mm long fleece consisting of 100 parts glass fibre (diameter 0.49 to 0.58 μm, length 1000 μm) and 5 parts polyvinyl alcohol fibres (Kuralon VPB 105-2 from Kuraray) having a weight per unit area of about 180 g/m$^2$ as a liquid collection zone (waste) 2 (suction zone D)
- 1.5 cm long cellulose nitrate membrane (type CN 11301 from Sartorius, Germany) as a chromatography membrane 3 containing the detection and control zone (detection zone C)
- a 1.5 mm thick and 13 mm long fleece consisting of 100 parts glass fibres and 10 parts polyvinyl alcohol fibres (both fibres analogous to the liquid collection zone) having a weight per unit area of about 180 g/m$^2$ as a blood separation fleece 4 (erythrocyte separation zone B)
- and two 18 mm or 20 mm long fleeces consisting of 80 parts polyester fibres, 20 parts rayon staple and 20 parts polyvinyl alcohol fibres having a thickness of about 0.32 mm and a weight per unit area of about 80 g/m$^2$ (the manufacture of which is described in example 1 of the European Patent Document EP 0 326 135) containing gold conjugate (gold conjugate fleece 5) as a zone containing a labelled partner of the specific binding pair and containing biotin conjugate (biotin conjugate fleece 6) as a further zone containing the tagged partner of the specific binding pair.

An aqueous streptavidin solution (4.5 mg/ml) is applied by line metering onto the previously described cellulose nitrate membrane of the detection zone 3. The dosage for this is selected such that (metered amount 0.1 ml/min, web speed 3 m/min) a line with a width of about 0.4 mm is formed. This line 7 serves to detect the analyte to be determined and contains about 0.8 µg streptavidin per test strip.

An aqueous 1 mg/ml TnI polyhapten solution (for preparation of the polyhapten see below), a 1 mg/ml streptavidin solution or a 1:1 mixture of polyhapten solution and streptavidin solution (each containing 1 mg/ml) are applied at a distance of about 4 mm downstream of the streptavidin line under identical metering conditions. These lines 8 are used to check the function of the test strip and contain either about 0.15 µg polyhapten and/or 0.15 µg streptavidin per test strip.

The membrane is subsequently dried in air.

The polyhapten is prepared as follows: A peptide with an amino acid sequence winch corresponds to the epitope containing the amino acids (aa) 27-43 of cardiac troponin I (see FEBS, Vol. 270; No. 1, 2; page 57-61: Molecular cloning of human cardiac troponin I using polymerase chain reaction) is prepared by classical peptide solid phase synthesis known to a person skilled in the art. A peptide residue consisting of β-alanine, ε-aminocaproic acid, β-alanine and cysteine is used as an N-terminal spacer for linkage to the carrier protein so that the peptide has a molecular weight of 1716.13.

The peptide is subsequently coupled by means of MH (BPLA)/SH peptide coupling to bovine plasma albumin as a carrier protein at a molar ratio of 10:1 (peptide to carrier protein).

The polyhapten is subsequently freeze dried in the presence of 40 mg/ml trehalose and dissolved in demineralised water for the line metering.

The polyhapten is referred to in the following as PH, TnI (27-43) [UZU-Cys-43] amide.

The gold conjugate fleece 5 is prepared as follows: A gold sol having an average particle diameter of about 40 nm is prepared according to the method of Frens (Frens, G., Preparation of gold dispersions varying particle size: controlled nucleation for the regulation of the particle size in monodisperse gold suspensions in Nature; Physical Science 241 (1973), 20-22) by reducing a 0.01% by weight tetrachloroauric acid solution with trisodium citrate while boiling.

The antibody-gold conjugate is prepared according to the method of Roth, J. (The colloidal gold marker system for light and electron microscopic cytochemistry in Bullock, G. R. and Petrusz, P. Eds., Techniques in Immunocytochemistry Vol. 2, New York, Academic Press 1983, 216-284).

For this the pH of the gold sol is adjusted with 0.2 M $K_2CO_3$ after cooling the gold sol solution to room temperature such that it is about 0.5 pH units above the isoelectric point of the <cTn I> antibody. The monoclonal <cTn I> mouse antibody with the clone name M155 can be obtained commercially from the HyTest Company under the catalogue No. 4T21 (Turku, Finland). This monoclonal antibody recognizes the cTn I epitope aa 27-43.

The optical density (OD) of the gold sol (absorbance at 525 nm and 1 cm clearance) is typically 1.0. The <cTn I> antibody is added in an aqueously dissolved form such that its concentration is 1.2 µg/ml after addition to the gold sol solution. After stirring for 30 minutes at room temperature, the gold conjugate is saturated by adding a highly concentrated bovine plasma albumin solution (final concentration in the conjugate solution 1 mg/ml).

After a further 30 minutes stirring at room temperature, the post-saturated gold conjugate is concentrated to an optical density of typically 20 by ultrafiltration through a 30 KDa membrane against a 20 mM Tris buffer pH 7.0. 100 µM Brij 35 and 0.05% by weight $NaN_3$ are subsequently added to the conjugate solution and it is stored while rolling at 4° C. until use.

The gold conjugate fleece 5 is impregnated with the following impregnation solution: 50 mM HEPES pH 7.5; 1.0% by weight bovine plasma albumin; 1.0% sucrose, 0.1% Tween 20, and MAB<cTn I>M155-IgG-40 nm gold sol conjugate OD 4.5.

For this purpose the polyester rayon staple-polyvinyl alcohol mixed fleece is firstly pulled through a trough containing the impregnation solution, subsequently squeezed out through two stainless steel rollers arranged at a spacing of 250 µm and finally dried at 60° C. by a circulating air drier. The amount of impregnation solution taken up by the fleece is typically 240 ml/m$^2$ under the described conditions.

The biotin conjugate fleece is prepared as follows (6): The monoclonal <cTn I> mouse antibody having the clone name 16A11 (commercially available under the catalogue No. 4T21 from the HyTest Company) is used to prepare the biotin conjugate. This monoclonal antibody recognizes the cTn I epitope as 87-91.

A succinimide ester derivative of biotin is added in an 8-fold molar excess to a solution of 10 mg/ml IgG in 0.1 M potassium phosphate pH 8.5. The mixture is incubated for 90 minutes at 25° C. while stirring. The reaction is stopped by adding lysine to the solution to a final concentration of 10 mM. The excess biotinylation reagent is removed by dialysis and stored at −70° C. until use in the presence of 6% by weight sucrose.

The biotin conjugate fleece 6 is impregnated with the following impregnation solution: 20 mM Tris pH 7.2, 50 mM NaCl, 1.0% by weight bovine plasma albumin, 1.0% by weight sucrose, 0.1% by weight Tween 20, and 7 mg/l MAB <cTn I>M-16A11-IgG biotin (XOSu 8:1). It was impregnated and dried under similar conditions to those used for the preparation of the gold conjugate fleece.

b.) Evaluation of the Test Strips

The following three test strip variants which only differed in the composition of the control line 8 were manufactured according to the method described under a). The solutions for preparing the control lines 8 contained the following in the three variants:

Variant 1: 1 mg/ml polyhapten [pH, Tn I (27-43)]; test strip with a classical control line.

Variant 2: 1 mg/ml streptavidin; test strip with second detection line reagent as a control line.

Variant 3: 1 mg/ml polyhapten and 1 mg/ml streptavidin; test strip with a control line according to the invention.

As already described above, all test strip variants have an identical detection line 7 containing 4.5 mg/ml streptavidin.

cTn I-Negative donor blood to which increasing amounts of cTn I-C-T complex (commercially available as catalogue No. 8T62 from HyTest) were added, was used to evaluate the test strips. For this purpose 150 µl spiked donor blood was added by pipette per test strip as a sample to the biotin conjugate fleece 6 which also served as the sample application zone and the test result was evaluated visually after 15 minutes for the appearance of a detection line and a control line and also evaluated by reflection photometry using a measuring instrument (Roche Cardiac Reader, Roche Diagnostics GmbH, Order No. 1902229) to quantify the line intensity. In this case 100% reflectance represents the absence of a line in the detection or control line zone whereas 20% reflectance represents deep dark red lines at which intensity the detection system of the measuring device is in color saturation.

The results are summarized in the following table.

| cTn I concentrations | Signal (in [% reflectance] or visually* positive (+) or negative (−)) | | | |
|---|---|---|---|---|
| | detection | Control line variant | | |
| [ng/ml] | line | 1 | 2 | 3 |
| 0 | 100 (−) | 20 (+) | 100 (−) | 20 (+) |
| 1 | 65 (+) | 30 (+) | 80 (+) | 20 (+) |
| 10 | 25 (+) | 45 (+) | 60 (+) | 20 (+) |
| 50 | 18 (+) | 96 (+/−) | 40 (+) | 35 (+) |
| 250 | 30 (+) | 98 (−) | 65 (+) | 65 (+) |
| 1000 | 98 (−) | 100 (−) | 98 (−) | 98 (−) |

*The speciciﬁcation (−) or (+) refers to the visual result classiﬁcation:
(−) = no visible line
(+) = visible line The results are interpreted as follows:
Detection Line:

As expected the intensity of the detection line firstly increases with increasing analyte concentrations (decrease of the reflectance values between 1 ng/ml and 50 ng/ml cTn I), passes an intensity maximum (18% reflectance i.e. colour saturation) and then decreases again at extremely high analyte concentrations due to a high-dose Hook effect caused by the sandwich format. The said high-dose Hook effect results in reflectance values of almost 100% (visually negative) on the detection line of the test strip at 1000 ng/ml cTn I and thus in a false-negative detection line.
Variant 1: "Classical Control Line":

In the absence of analyte the gold conjugate accumulates almost quantitatively on the control line by binding via the M155 antibody/polyhapten (aa 27-43) (20% reflectance). As the analyte concentration increases, the colour intensity of the control line decreases because, on the one hand, a larger portion of the gold conjugate is captured at the detection line in the form of a sandwich complex and because the portion of gold conjugate that is not captured at the detection line is already saturated due to the increased concentration of analyte that is present and thus can no longer be adequately bound by the polyhapten of the control line. In this case the chromatographed gold conjugate migrates across the detection line and across the control line into the waste fleece 2 which is situated downstream thereof.

Above 50 ng/ml cTn I in the sample, this results in a failure of the control line (visually negative) although the detection line is still clearly positive at this concentration and also at 250 ng/ml.

However, due to the absence of the control line the user must in this case erroneously assume the test result invalid.

This finding corresponds to the prior art and thus illustrates the limitations of a classical polyhapten control line.
Variant 2: "Second Detection Line as a Control Line":

The second streptavidin detection line which is to be regarded as a control line of course fails in the absence of analyte (with regard to its function as a control line) since no sandwich complex has formed. The test result would therefore be regarded as invalid although the negative first detection line correctly reflects the absence of the analyte.

In the presence of analyte the streptavidin control line like the detection line detects the formed sandwich complex although less intensively since most of the sandwich complex that is formed has already been bound upstream by the detection line.

At very high analyte concentrations (1000 ng/ml cTn I) the control line also fails in addition to the detection line since both are subject to the same mechanism (cf., above with regard to the high-dose Hook effect).
Variant 3: "Control Line According to the Invention"

As shown by the measurements and visual classifications in the table, this control line indicates a correct test result (by means of the polyhapten gold conjugate mechanism) in the absence of analyte.

In the mid concentration range the control line generates signals by both immunological mechanisms which are additive.

In the upper concentration range (50-250 ng/ml cTn I) the control line generates the measured signal mainly by the streptavidin-biotin mechanism (the classical polyhapten control line is in this case already in analyte saturation and therefore fails). When a high-dose Hook effect is present at the detection line (1000 ng/ml cTn I), the control line also fails which is as desired.

The sum of these properties shows that this novel control line mechanism is superior to the previously known technical embodiments.

It is known that terms like "preferably", "commonly", and "typically", are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically although some aspects of the present invention are identified herein as preferred or particularly advantageous, it is contemplated that the present invention is not necessarily limited to these preferred aspects of the invention.

What is claimed is:

1. A method for identifying the presence of the Hook effect during the immunochromotographic determination of an analyte in a liquid sample, the method comprising:
contacting the sample with a reagent zone of an immunochromatographic device comprising the reagent zone, a detection zone and a control line, and allowing the sample to migrate from the reagent zone to the detection zone and the control line, wherein
the reagent zone comprises a labeled conjugate comprising an analyte binding partner and a label in migratable form and is dissolvable in the liquid sample;
the detection zone comprises a first permanently immobilized binding partner for the analyte; and
the control line comprises a second permanently immobilized binding partner for the analyte or complexes containing the analyte and a permanently immobilized binding partner for the labeled conjugate, and
detecting the signal associated with the labeled conjugate immobilized in the detection zone and the control line, wherein the lack of signal in the detection zone and the control line indicates the presence of the Hook effect.

2. The method of claim 1, wherein the permanently immobilized binding partner for the labeled conjugate competes with the analyte for binding to the labeled conjugate.

3. The method of claim 1, wherein the permanently immobilized binding partner for the labeled conjugate in the control line is a polyhapten.

4. The method of claim 1, wherein the permanently immobilized binding partners for the analyte in the detection zone and in the control line are the same.

5. The method of claim 1, wherein the permanently immobilized binding partners for the analyte in the detection zone and in the control line are different.

6. The method of claim 1, wherein the first permanently immobilized binding partner for the analyte in the detection zone is an antibody or an immunologically active fragment of an antibody.

7. The method of claim 1, wherein the second permanently immobilized binding partner for the analyte in the control line is an antibody or an immunologically active fragment of an antibody.

8. The method of claim 1, wherein the first permanently immobilized binding partner for the analyte in the detection zone is a hapten or a polyhapten.

9. The method of claim 1, wherein the second permanently immobilized binding partner for the analyte in the control line is a hapten or a polyhapten.

10. The method of claim 1, wherein the label can be detected visually, optically or electrochemically.

11. A method for identifying the presence of a Hook effect during the immunochromotographic determination of an analyte in a liquid sample, the method comprising:
  contacting the sample with an immunochromatographic device comprising a combination of binding zones for detection of the analyte and the determination of the Hook effect, the combination consisting of a reagent zone, a detection zone and a control line, and allowing the sample to migrate from the reagent zone to the detection zone and the control line, wherein
    the reagent zone comprises a labeled conjugate comprising an analyte binding partner and a label in migratable form and is dissolvable in the liquid sample;
    the detection zone comprises a first permanently immobilized binding partner for the analyte; and
    the control line comprises a second permanently immobilized binding partner for the analyte or complexes containing the analyte and a permanently immobilized binding partner for the labeled conjugate, and
  detecting the signal associated with the labeled conjugate immobilized in the detection zone and the control line, wherein the lack of signal in the detection zone and the control line indicates the presence of the Hook effect.

* * * * *